(12) United States Patent
Wang et al.

(10) Patent No.: US 10,542,880 B2
(45) Date of Patent: Jan. 28, 2020

(54) THREE-DIMENSIONAL CONTOUR SCANNING DEVICE

(71) Applicant: Qisda Corporation, Taoyuan (TW)

(72) Inventors: Ching-Huey Wang, Hsinchu County (TW); Ming-Kuen Lin, Taoyuan (TW); Ying-Fang Lin, Taoyuan County (TW)

(73) Assignee: QISDA CORPORATION, Taoyuan (TW)

( * ) Notice: Subject to any disclaimer, the term of this patent is extended or adjusted under 35 U.S.C. 154(b) by 47 days.

(21) Appl. No.: 15/726,490

(22) Filed: Oct. 6, 2017

(65) Prior Publication Data

US 2018/0098691 A1 Apr. 12, 2018

(30) Foreign Application Priority Data

Oct. 11, 2016 (CN) .......................... 2016 1 0886262

(51) Int. Cl.
*A61B 1/24* (2006.01)
*A61C 9/00* (2006.01)
*G02B 27/28* (2006.01)

(52) U.S. Cl.
CPC .............. *A61B 1/24* (2013.01); *A61C 9/0053* (2013.01); *G02B 27/288* (2013.01)

(58) Field of Classification Search
CPC . G01B 11/2513; G01B 11/24; G01B 11/2518; G01B 11/0608; G01B 11/25; G01B 11/2504; G01B 11/2509; G01B 11/30; G01B 2210/52; G01B 2210/58; G01B 11/02; G01B 11/03; G01B 11/04; G01B 11/0691; G01B 11/10; G01B 11/245; G01B 11/303; G01B 21/042; G01B 21/045; G01B 21/20; G01B 21/32; G01B 5/0014; G01B 9/02091; G02B 27/0093; G02B 27/017; G02B 2027/0178; G02B 2027/0138; G02B 2027/014;

(Continued)

(56) References Cited

U.S. PATENT DOCUMENTS 9,693,839 B2 * 7/2017 Atiya .................... A61C 9/0053
2008/0062429 A1 * 3/2008 Liang ................. A61B 1/00039
356/497

(Continued)

FOREIGN PATENT DOCUMENTS

CN        10155316 A     10/2009
CN        105137596 A    12/2015

(Continued)

OTHER PUBLICATIONS

Office action of counterpart application by State Intellectual Property Office of the People's Republic of China dated Jan. 4, 2019.

*Primary Examiner* — Michael P Stafira (57) ABSTRACT

A three-dimensional contour scanning device including an image sensing element, a light source and a single polarity element is provided. The light source is used for emitting a projection light to a to-be-scanned object through a projection optical path. The projection light reflected from the to-be-scanned object becomes an imaging light further reflected to the image sensing element through an image-formed optical path. The single polarity element is disposed on the projection optical path and the image-formed optical path.

17 Claims, 4 Drawing Sheets

(58) Field of Classification Search
CPC ........ G02B 2027/0187; G02B 26/0875; G02B 26/10; G02B 27/0905; G02B 27/0961; G02B 7/023; G02B 7/08; G02B 21/0028; G02B 21/008; G02B 13/0005; G02B 26/125; G02B 27/288; G01J 3/0208; G01J 3/0224; G01J 3/0237; G01J 3/0278; G01J 3/508; G01J 3/51; G01J 3/513; G01J 5/10; A61B 5/0088; A61B 1/24; A61B 2090/306; A61B 5/1079; A61B 5/4547; A61B 6/032; A61B 5/0062; A61B 5/0095; A61B 5/1077; A61B 1/00172; A61B 2034/2057; A61B 2034/2065; A61B 2090/371; A61B 34/20; A61B 5/0059; A61B 5/0068; A61B 5/0073; A61B 5/0075; A61B 5/0082; A61B 5/0091; A61B 5/015; A61B 5/02007; A61B 5/1036; A61B 5/14542; A61B 5/14546; A61B 5/4312; A61B 5/444; A61B 5/4848; A61B 6/469; A61B 8/485; A61B 1/00009; A61B 2034/105; A61B 2034/2048; A61B 2034/2051; A61B 2034/2072; A61B 2090/064; A61B 2090/309; A61B 2090/3614; A61B 2090/3937; A61B 2090/3958; A61B 2090/3991; A61B 2562/0233; A61B 2562/046; A61B 2576/00; A61B 2576/02; A61B 5/0077; A61B 5/0261; A61B 5/0507; A61B 5/14551; A61B 5/14552; A61B 5/412; A61B 5/445; A61B 5/447; A61B 5/4884; A61B 5/7275; A61B 5/742; A61B 6/0492; A61B 6/14; A61B 6/488; A61B 6/501; A61B 6/545; A61B 6/547; A61B 18/02; A61B 1/00006; A61B 1/00013; A61B 1/00016; A61B 1/00018; A61B 1/00101; A61B 1/00147; A61B 1/00197; A61B 1/045; A61B 1/06; A61B 1/0661; A61B 1/0684; A61B 1/247; A61B 2018/00511; A61B 2018/00541; A61B 2018/00577; A61B 2018/00642; A61B 2018/00982; A61B 2018/0293; A61B 2034/104; A61B 2034/107; A61B 2090/365; A61B 2090/376; A61B 2090/3764; A61B 2090/502; A61B 34/10; A61B 34/25; A61B 5/0035; A61B 5/0037; A61B 5/004; A61B 5/0046; A61B 5/0084; A61B 5/1076; A61B 5/1127; A61B 5/682; A61B 5/6888; A61B 5/6889; A61B 5/6891; A61B 5/6892; A61B 5/721; A61B 5/7242; A61B 5/7253; A61B 5/7257; A61B 5/744; A61B 6/022; A61B 6/0457; A61B 6/08; A61B 6/145; A61B 6/447; A61B 6/4482; A61B 6/463; A61B 6/465; A61B 6/466; A61B 6/486; A61B 6/487; A61B 6/5235; A61B 6/5247; A61B 6/542; A61B 6/582; A61B 6/584; A61B 8/00; A61B 8/13; A61B 90/10; A61B 90/11; A61B 90/18; A61B 90/37; G01N 29/2418; G01N 21/1702; G01N 2291/02836; G01N 2291/02872; G01N 29/0681; G01N 2021/3144; G01N 2021/4709; G01N 21/31; G01N 21/359; G01N 21/474; G01N 21/4795; G01N 21/49; G01N 2201/06113; G01N 2021/8472; G01N 2021/8663; G01N 2035/0091; G01N 21/4738; G01N 21/55; G01N 21/59; G01N 21/8422; G01N 21/86; G01N 21/954; G01N 2291/02475; G01N 2291/2638; G01N 23/20008; G01N 29/0672; G01N 29/265; G01N 33/491; G01N 35/00

See application file for complete search history.

(56) References Cited

U.S. PATENT DOCUMENTS

| | | | |
|---|---|---|---|
| 2008/0118886 A1* | 5/2008 | Liang ................... | A61B 5/0088 433/29 |
| 2011/0194121 A1* | 8/2011 | Ertl ...................... | A61B 5/0088 356/610 |
| 2015/0164335 A1* | 6/2015 | Van Der Poel ...... | A61C 9/0053 433/29 |
| 2016/0163115 A1* | 6/2016 | Furst ....................... | G06T 19/20 433/29 |
| 2017/0156826 A1* | 6/2017 | Eom ..................... | A61B 1/0019 |

FOREIGN PATENT DOCUMENTS

| | | |
|---|---|---|
| CN | 205286293 U | 6/2016 |
| KR | 10-2015-0056711 * | 4/2015 |

* cited by examiner

THREE-DIMENSIONAL CONTOUR SCANNING DEVICE

This application claims the benefit of People's Republic of China application Serial No. 201610886262.1, filed Oct. 11, 2016, the subject matter of which is incorporated herein by reference.

BACKGROUND OF THE INVENTION

Field of the Invention

The invention relates in general to a contour scanning device, and more particularly to a three-dimensional contour scanning device.

Description of the Related Art

Conventional oral cavity scanner emits a projection light to the teeth inside the oral cavity, then the imaging light is reflected from the teeth is analyzed to obtain a surface contour of the teeth. However, some of the projection lights not completely reflected from the teeth are refracted to the inside of the teeth and then are emitted off the teeth. The refraction light will affect the accuracy of the surface contour of the teeth.

Therefore, it has become a prominent task for those who are versed in the technology field of the invention to resolve the negative influence caused by the refraction light.

SUMMARY OF THE INVENTION

The invention is directed to a three-dimensional contour scanning device capable of resolving the abovementioned problems.

According to one embodiment of the present invention, a three-dimensional contour scanning device including an image sensing element, a light source and a single polarity element is provided. The light source is used for emitting a projection light to a to-be-scanned object through a projection optical path. The projection light reflected from the to-be-scanned object becomes an imaging light further reflected to the image sensing element through an image-formed optical path. The single polarity element is disposed on the projection optical path and the image-formed optical path.

According to another embodiment of the present invention, a three-dimensional contour scanning device is provided. The three-dimensional contour scanning device includes a host, an image sensing element, a light source, a protrusion tube, a reflective element and the single polarizing element. The image sensing element is disposed inside the host. The light source is disposed inside the host. The protrusion tube is detachably connected to the host and has a first opening and a third opening opposite to the first opening, wherein the third opening is adjacent to the host. The reflective element is disposed inside the protrusion tube, wherein the first opening is adjacent to the reflective element. The single polarity element is disposed inside the protrusion tube.

The above and other aspects of the invention will become better understood with regard to the following detailed description of the preferred but non-limiting embodiment (s). The following description is made with reference to the accompanying drawings.

DETAILED DESCRIPTION OF THE INVENTION

Figure 1:
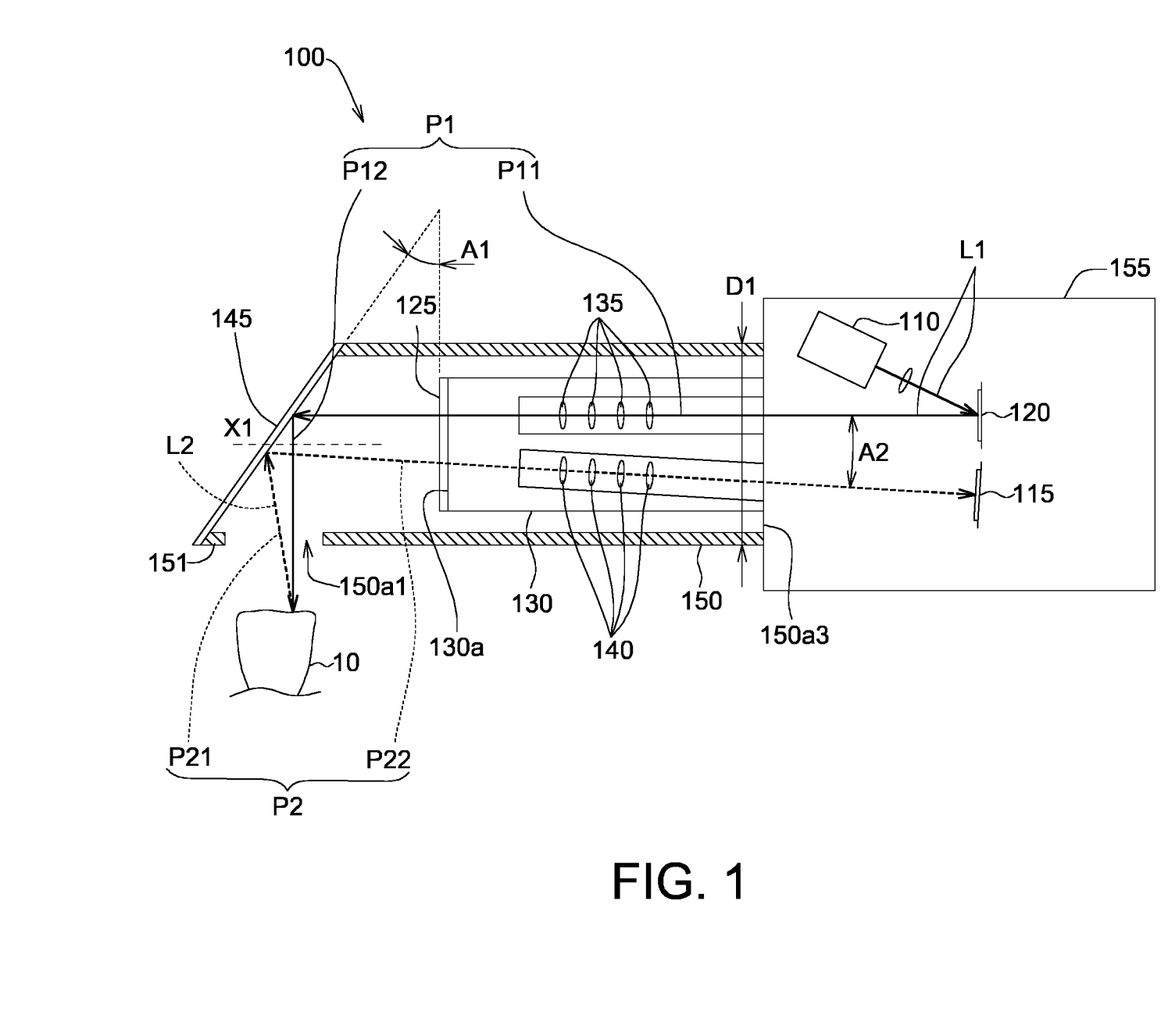
FIG. 1 is a schematic diagram of a three-dimensional contour scanning device according to an embodiment of the invention.

FIG. 1 is a schematic diagram of a three-dimensional contour scanning device 100 according to an embodiment of the invention. The three-dimensional contour scanning device 100, such as an oral cavity scanner, can scan the contour of the teeth inside the oral cavity. However, the three-dimensional contour scanning device 100 of the invention embodiment is not limited to an oral cavity scanner.

The three-dimensional contour scanning device 100 includes a light source 110, an image sensing element 115, an image generation element 120, a polarity element 125, a barrel 130, a projection imaging module 135, a capturing optical module 140, a reflective element 145, a protrusion tube 150 and a host 155.

The light source 110, which can be realized by a light emitting diode or a laser light source, is used for emitting a projection light L1 (illustrated in bold lines) to a to-be-scanned object 10 through a projection optical path P1, wherein the to-be-scanned object 10 can be realized by teeth or other to-be-scanned object having a three-dimensional contour. The projection light L1 reflected from the to-be-scanned object 10 becomes an imaging light L2 (illustrated in bold lines) reflected to the image sensing element 115 through an image-formed optical path P2. In an embodiment, the image sensing element 115 can be realized by a complementary metal-oxide-semiconductor (CMOS).

The image generation element 120 is located on the projection optical path P1 and is used for changing a projection pattern of the projection light L1. The projection pattern is deformed after the projection light L1 is reflected from the to-be-scanned object 10. The image sensing element 115 or an analyzer (not illustrated) electrically connected to the image sensing element 115 can analyze the deformed projection pattern to obtain a three-dimensional contour of the to-be-scanned object 10. In an embodiment, the image generation element 120 can be realized by a digital micro-mirror device (DMD) or a display such as a liquid crystal display (LCD).

In the present embodiment, the single polarity element 125 is disposed on the projection optical path P1 and the image-formed optical path P2, and the projection light L1 passing through the polarity element 125 will become a first linearly polarized light. The first linearly polarized light, having been reflected from the to-be-scanned object, will pass through the same polarity element 125 and become a second linearly polarized light. Since the projection light L1 and the imaging light L2 pass through the same polarity element 125, the first linearly polarized light and the second linearly polarized light have the same polarizing direction. In comparison to the three-dimensional contour scanning device using multiple polarizing elements, the three-dimensional contour scanning device 100 of the invention embodiment uses only one single polarity element 125, therefore the cost can be reduced and the complexity of optical path can be simplified. In an embodiment, the polarity element 125 can be realized by a polarizer.

Since the imaging light L2 passes through the polarity element 125, the surface contour of the to-be-scanned object 10 can be obtained with larger accuracy. The imaging light L2 refracted from the interior of the to-be-scanned object 10 (the polarizing direction changes) will be fully or partly filtered off by the polarity element 125, and only the imaging light L2 reflected from the surface of the to-be-scanned object 10 (the polarizing direction does not change) can pass through the polarity element 125. In the invention, although the imaging light L2 is still refracted from the interior of the to-be-scanned object 10, the imaging light L2 refracted from the interior of the to-be-scanned object 10 is filtered off, therefore the surface contour of the to-be-scanned object 10 still can be obtained with larger accuracy.

Moreover, the light source 110, the image sensing element 115 and the image generation element 120 all can be disposed inside the host 155.

The barrel 130 is disposed inside the protrusion tube 150. The barrel 130 is fixedly connected to the host 155 and has a second opening 130a. In the present embodiment, the polarity element 125 can be disposed in the second opening 130a of the barrel 130, such that the polarity element 125 is fixedly to the host 155 through the barrel 130. However, the invention is not limited thereto.

The projection imaging module 135 may include at least one lens for successfully emitting the projection light L1 to the reflective element 145. Similarly, the capturing optical module 140 may include at least one lens for successfully emitting the imaging light L2 to the image sensing element 115. Besides, the projection imaging module 135 and the capturing optical module 140 can be disposed on the barrel 130 or inside the host 155.

As indicated in FIG. 1, the reflective element 145 is disposed inside the terminal end 151 of the protrusion tube 150 and forms an angle of 45° with the axis X1 of the protrusion tube 150. The reflective element 145 is also located on the projection optical path P1 and the image-formed optical path P2 for reflecting the projection light L1 to a to-be-scanned object 10, and the imaging light L2 reflected from the to-be-scanned object 10 is further reflected to the image sensing element 115. The protrusion tube 150 has a first opening 150a1 located at a terminal end 151 of the protrusion tube 150. The projection light L1 and the imaging light L2 pass through the protrusion tube 150 via the first opening 150a1.

As indicated in FIG. 1, the projection optical path P1 includes a first sub-projection optical path P11 and a second sub-projection optical path P12. The image-formed optical path P2 includes a first sub-imaging optical path P21 and a second sub-imaging optical path P22. The projection light L1 is emitted to the reflective element 145 through the first sub-projection optical path P11 and is further reflected to a to-be-scanned object 10 from the reflective element 145 through the second sub-projection optical path P12. The projection light L1 reflected from the to-be-scanned object 10 becomes an imaging light L2. The imaging light L2 is reflected to the reflective element 145 from the to-be-scanned object 10 through the first sub-imaging optical path P21 and is further reflected to the image sensing element 115 from the reflective element 145 through the second sub-imaging optical path P22. In the present embodiment, the single polarity element 125 is located on the first sub-projection optical path P11 and the second sub-imaging optical path P22 such that the projection light L1 and the imaging light L2 can pass through the polarity element 125.

As indicated in FIG. 1, the protrusion tube 150 has a third opening 150a3. The reflective element 145 is projected to the third opening 150a3 along the first projection area. In the present embodiment, the single polarity element 125 is located within the first projection area. The first projection area refers to the range of projection path through which the reflective element 145 is projected to the third opening 150a3. Besides, the angle A1 included between the reflective element 145 and the polarity element 125 is 45°. The angle A1 included between the reflective element 145 and the polarity element 125 is not subjected to specific restrictions, and any angle will do as long as the polarity element 125 is located within the first projection area.

As indicated in FIG. 1, the angle A2 included between the first sub-projection optical path P11 and the second sub-imaging optical path P22 is smaller than 15°, thus the outer diameter of the protrusion tube 150 can be reduced. The larger the angle A2, the larger the outer diameter D1 of the protrusion tube 150 is required. Conversely, the smaller the angle A21, the smaller the outer diameter D1 of the protrusion tube 150 is required. Since the angle A2 is smaller than 15°, the protrusion tube 150 can enter the oral with a suitable outer diameter D1. For example, the cross-section of the protrusion tube 150 has a circular shape, and the outer diameter D1 of the protrusion tube 150 ranges 0≤45 mm. Or, the cross-section of the protrusion tube 150 is not circular but has a rectangular shape whose edges and diagonal ranges 0≤45 mm.

The protrusion tube 150 is detachably connected to the host 155. The polarity element 125 and the reflective element 145 can be disposed inside the protrusion tube 150, and can be detached from or connected to the host 155 along with the protrusion tube 150, such that the protrusion tube 150 becomes an a disposable element. Since the protrusion tube 150 is a disposable element, when different patients' to-be-scanned objects 10 (such as teeth) need to be scanned, the protrusion tube 150 can be replaced to meet different medical requirements, such as the sizes of the patients' oral cavity, and the patients' gender and/or conditions.

Figure 2:
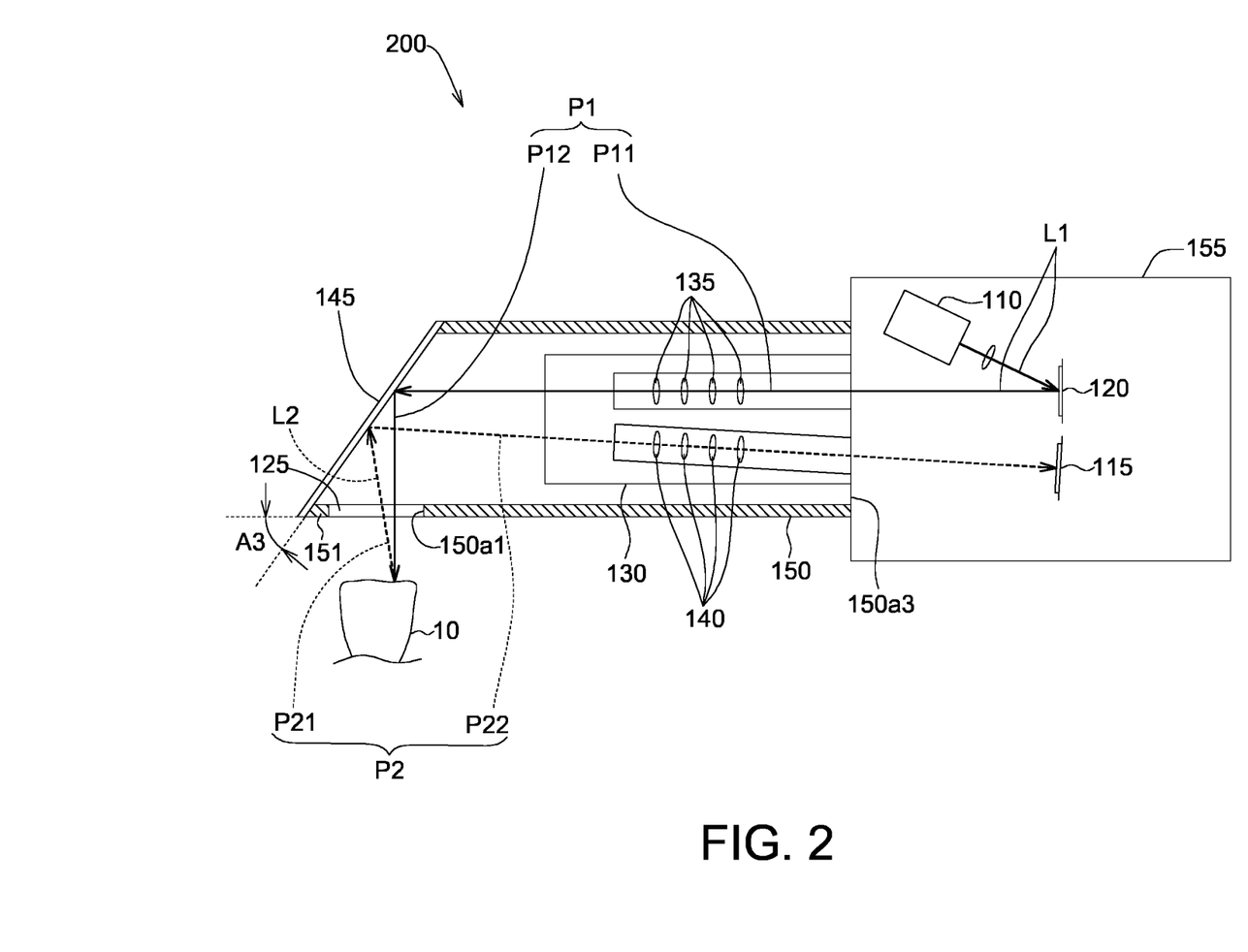
FIG. 2 is a schematic diagram of a three-dimensional contour scanning device according to another embodiment of the invention.

FIG. 2 is a schematic diagram of a three-dimensional contour scanning device 200 according to another embodiment of the invention.

The three-dimensional contour scanning device 200 includes a light source 110, an image sensing element 115, an image generation element 120, a polarity element 125, a projection imaging module 135, a capturing optical module 140, a reflective element 145, a barrel 130, a protrusion tube 150 and a host 155.

Unlike the three-dimensional contour scanning device 100 of previous embodiments, the single polarity element 125 of the three-dimensional contour scanning device 200 of the present embodiment is located on the second sub-projection optical path P12 and the first sub-imaging optical path P21. Since the single polarity element 125 is located on the second sub-projection optical path P12 and the first sub-imaging optical path P21, the projection light L1 and the imaging light L2 pass through the same polarity element 125, the three-dimensional contour of the to-be-scanned object 10 can be obtained with larger accuracy. In comparison to the three-dimensional contour scanning device using multiple polarizing elements, the three-dimensional contour scanning device 200 of the invention uses only one single polarity element 125, therefore the cost can be reduced and the complexity of optical path can be simplified.

In greater details, the protrusion tube 150 has a first opening 150a1 located at the terminal end 151 of the protrusion tube 150. The projection light L1 is emitted to the to-be-scanned object 10 through the first opening 150a1. The polarity element 125 is disposed inside the first opening 150a1 or covers the first opening 150a1, such that the projection light L1 is also emitted to the to-be-scanned object 10 through the polarity element 125. As indicated in FIG. 2, the reflective element 145 is projected to the first opening 150a1 along the second projection area. In the present embodiment, the single polarity element 125 is located within the second projection area. The second projection area refers to the range of projection path through which the reflective element 145 is projected to the first opening 150a1. The angle A3 included between the reflective element 145 and the polarity element 125 is 45° is not subjected to specific restrictions, and any angle will do as long as the polarity element 125 is located within the second projection area.

Figure 3:
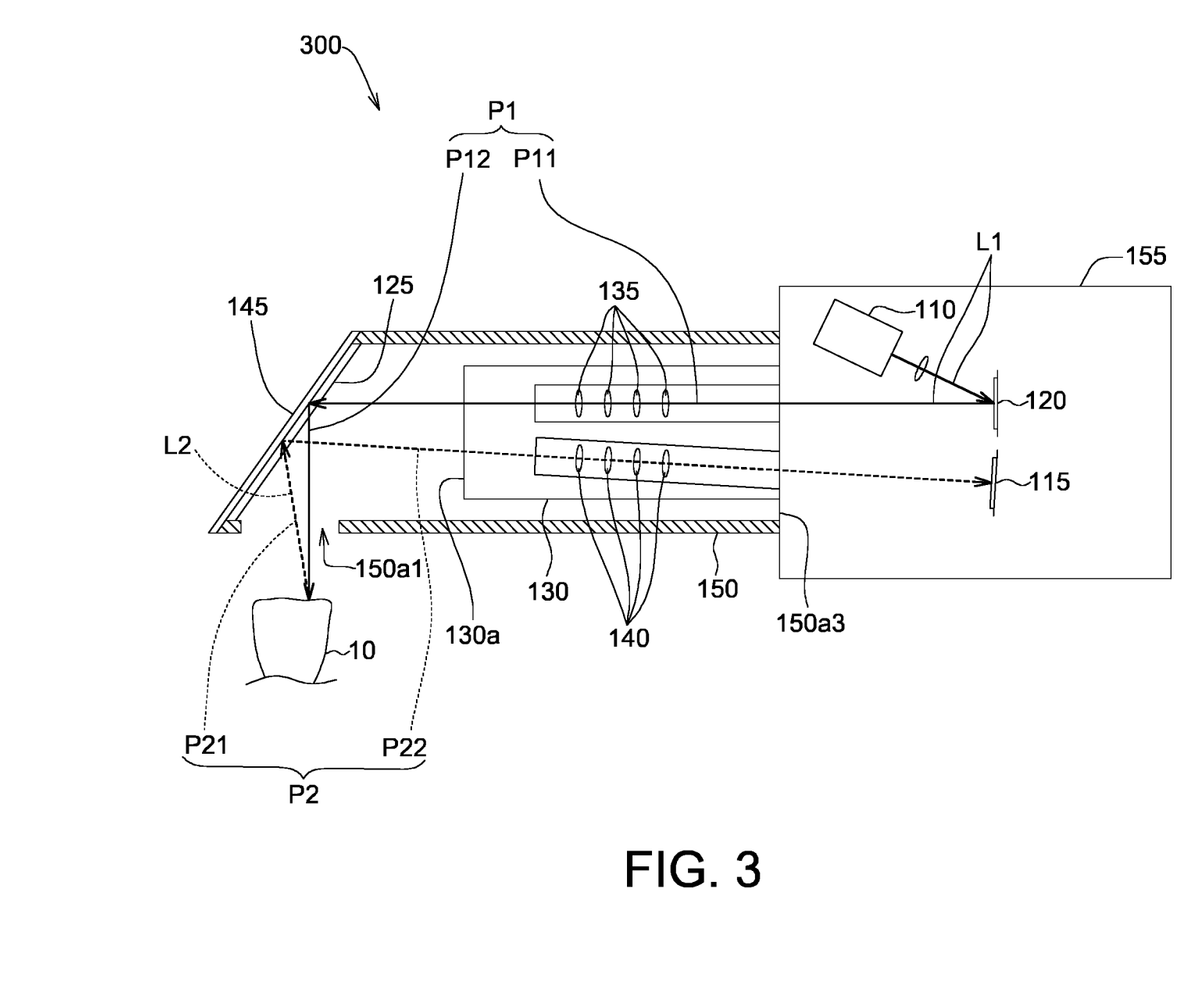
FIG. 3 is a schematic diagram of a three-dimensional contour scanning device according to another embodiment of the invention.

FIG. 3 is a schematic diagram of a three-dimensional contour scanning device 300 according to another embodiment of the invention.

The three-dimensional contour scanning device 300 includes a light source 110, an image sensing element 115, an image generation element 120, a polarity element 125, a barrel 130, a projection imaging module 135, a capturing optical module 140, a reflective element 145, a protrusion tube 150 and a host 155.

Unlike the three-dimensional contour scanning device 100 of previous embodiment, the single polarity element 125 of the three-dimensional contour scanning device 100 of the present embodiment is located on the first sub-projection optical path P11, the second sub-projection optical path P12, the first sub-imaging optical path P21 and the second sub-imaging optical path P22. Since the single polarity element 125 is located on the first sub-projection optical path P11, the second sub-projection optical path P12, the first sub-imaging optical path P21 and the second sub-imaging optical path P22, the projection light L1 and the imaging light L2 can pass through the same polarity element 125, and the three-dimensional contour of the to-be-scanned object 10 can be obtained with larger accuracy. In comparison to the three-dimensional contour scanning device using multiple polarizing elements, the three-dimensional contour scanning device 300 of the invention uses only one single polarity element 125, therefore the cost can be reduced and the complexity of optical path can be simplified.

The reflective element 145 and the polarity element 125 are disposed inside the protrusion tube 150, and the reflective element 145 and the polarity element 125 are substantially disposed in parallel and adjacent to each other. The reflective element 145 and the polarity element 125 can be attached together or can be adjacent to each other but not attached together. However, the invention does not restrict the disposition of the reflective element 145 and the polarity element 125. The reflective element 145 and the polarity element 125 can be attached together or adjacent to each other but not attached together, and any disposition of the reflective element 145 and the polarity element 125 will do as long as the polarity element 125 is located within the first projection area and the second projection area.

Figure 4:
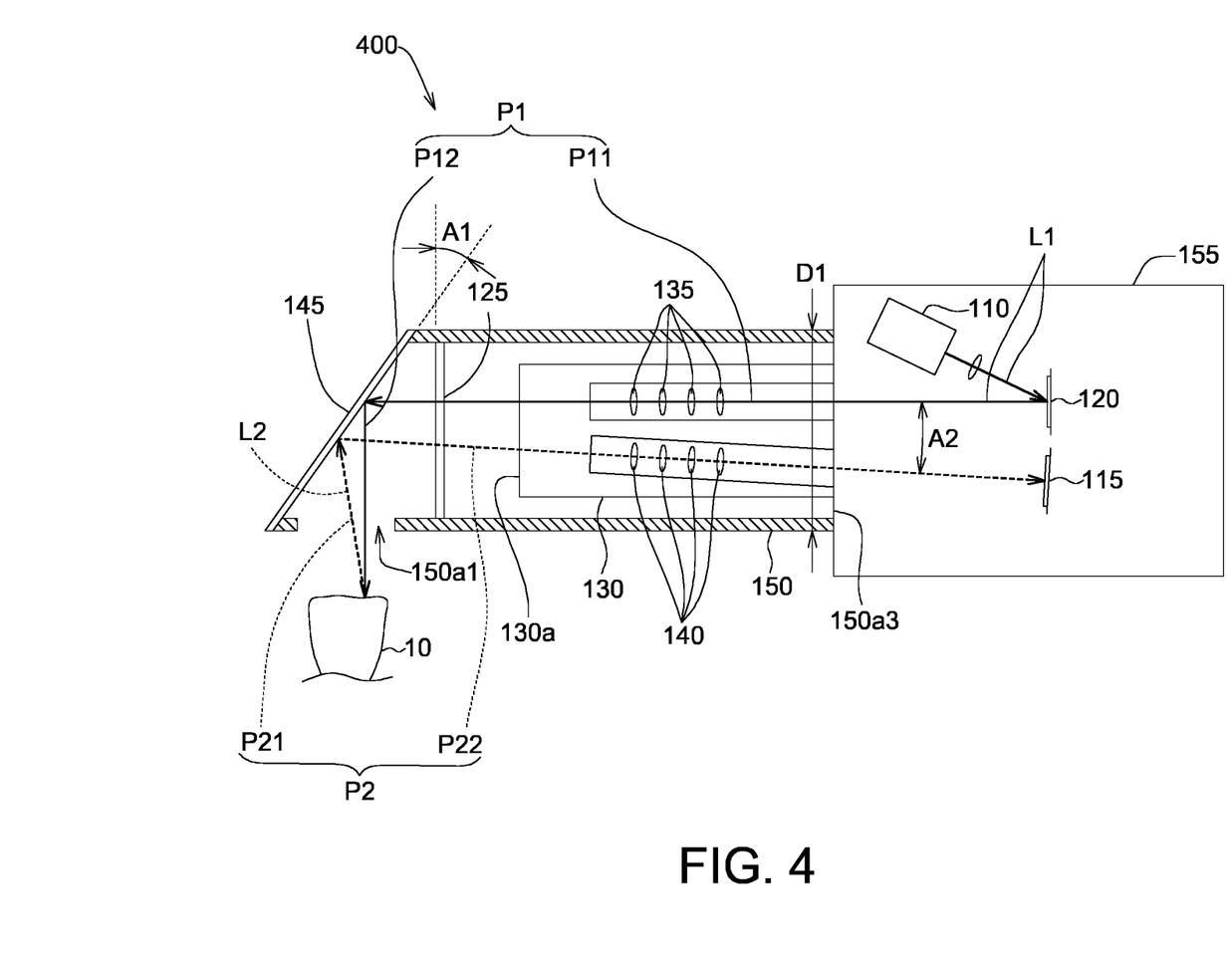
FIG. 4 is a schematic diagram of a three-dimensional contour scanning device according to another embodiment of the invention.

FIG. 4 is a schematic diagram of a three-dimensional contour scanning device 400 according to another embodiment of the invention. The three-dimensional contour scanning device 400 includes a light source 110, an image sensing element 115, an image generation element 120, a polarity element 125, a barrel 130, a projection imaging module 135, a capturing optical module 140, a reflective element 145, a protrusion tube 150 and a host 155. The three-dimensional contour scanning device 400 of the present embodiment and the three-dimensional contour scanning device 100 have similar features but are different in that that the polarity element 125 of the three-dimensional contour scanning device 400 of the present embodiment is located between the opening 130a of the barrel 130 and the reflective element 145 and is disposed on the inner wall of the protrusion tube 150 rather than inside the opening 130a of the barrel 130.

To summarize, the design of having the single polarity element of the three-dimensional contour scanning device of the invention located on the optical path of the projection light and the optical path of the imaging light reduces the cost and/or simplify the complexity of optical path complexity. Since the imaging light passes through the polarizing element, the surface contour of the to-be-scanned object can be obtained with larger accuracy. In an embodiment, the single polarity element can be disposed inside the protrusion tube, wherein the protrusion tube is detachably connected to the host, such that the polarity element can be detached from the host along with the protrusion tube. In another embodiment, the single polarity element can also be disposed inside the host directly or through another element such as a barrel.

While the invention has been described by way of example and in terms of the preferred embodiment (s), it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A three-dimensional contour scanning device, comprising:
   an image sensing element;
   a light source used for emitting a projection light to a to-be-scanned object through a projection optical path, wherein the projection light reflected from the to-be-scanned object becomes an imaging light and to the image sensing element through an image-formed optical path; and
   a single polarity element disposed on the projection optical path and the image-formed optical path;
   wherein the three-dimensional contour scanning device further comprises:
   a reflective element located on the projection optical path and the image-formed optical path;
   wherein the projection light travels to the reflective element through a first sub-projection optical path and is further reflected to the to-be-scanned object from the reflective element through a second sub-projection optical path; the imaging light is reflected to the reflective element from the to-be-scanned object through a first sub-imaging optical path and is further reflected to the image sensing element from the reflective element through a second sub-imaging optical path;
   wherein the single polarity element is located on the first sub-projection optical path and the second sub-imaging optical path.

2. The three-dimensional contour scanning device according to claim 1, further comprising:
   a host; and
   a protrusion tube detachably connected to the host and having a first opening;
   a reflective element disposed at a terminal end of the protrusion tube and an angle included between an axis of the protrusion tube and the reflective element is 45°;

wherein the projection light and the imaging light pass through the host via the first opening.

3. The three-dimensional contour scanning device according to claim 2, wherein the single polarity element and the reflective element are disposed in parallel.

4. The three-dimensional contour scanning device according to claim 3, the single polarity element and the reflective element are attached to each other.

5. The three-dimensional contour scanning device according to claim 2, wherein the first opening is located at the terminal end of the protrusion tube, and the single polarity element is disposed inside the first opening.

6. The three-dimensional contour scanning device according to claim 2, further comprising:
 a barrel fixedly connected to the host and having a second opening;
 wherein the single polarity element is disposed inside the second opening of the barrel.

7. The three-dimensional contour scanning device according to claim 2, wherein an angle include between the single polarity element and the reflective element is 45° and the single polarity element is located between the reflective element and the second opening.

8. The three-dimensional contour scanning device according to claim 1, further comprising:
 a reflective element, wherein an angle include between the single polarity element and the reflective element is 45°.

9. The three-dimensional contour scanning device according to claim 1, further comprising:
 a reflective element substantially disposed in parallel with the single polarity element.

10. The three-dimensional contour scanning device according to claim 1, further comprising:
 an image generation element located on the projection optical path and used for changing a projection pattern of the projection light.

11. A three-dimensional contour scanning device, comprising:
 a host;
 an image sensing element disposed inside the host;
 a light source disposed inside the host;
 a protrusion tube detachably connected to the host and having a first opening and a third opening opposite to the first opening, wherein the third opening is adjacent to the host;
 a reflective element disposed inside the protrusion tube, wherein the first opening is adjacent to the reflective element; and
 a single polarity element disposed inside the protrusion tube;
 where the three-dimensional contour scanning device further comprises:
 a reflective element located on the projection optical path and the image-formed optical path;
 wherein the projection light travels to the reflective element through a first sub-projection optical path and is further reflected to the to-be-scanned object from the reflective element through a second sub-projection optical path; the imaging light is reflected to the reflective element from the to-be-scanned object through a first sub-imaging optical path and is further reflected to the image sensing element from the reflective element through a second sub-imaging optical path;
 wherein (1). the single polarity element is located on the first sub-projection optical path and the second sub-imaging optical path, (2). the single polarity element is located on the second sub-projection optical path and the first sub-imaging optical path, or (3). the single polarity element is located on the first sub-projection optical path, the second sub-projection optical path, the first sub-imaging optical path and the second sub-imaging optical path.

12. The three-dimensional contour scanning device according to claim 11, wherein the reflective element is projected to the third opening along a first projection area, and the single polarity element is located in the first projection area.

13. The three-dimensional contour scanning device according to claim 11, wherein the reflective element is projected to the first opening along a second projection area, and the single polarity element is located in the second projection area.

14. The three-dimensional contour scanning device according to claim 11, wherein the reflective element is projected to the third opening along a first projection area, the reflective element is projected to the first opening along a second projection area, and the single polarity element is located in the first projection area and the second projection area.

15. A three-dimensional contour scanning device, comprising:
 an image sensing element;
 a light source used for emitting a projection light to a to-be-scanned object through a projection optical path, wherein the projection light reflected from the to-be-scanned object becomes an imaging light and to the image sensing element through an image-formed optical path; and
 a single polarity element disposed on the projection optical path and the image-formed optical path;
 wherein the three-dimensional contour scanning device further comprises:
 a reflective element located on the projection optical path and the image-formed optical path;
 wherein the projection light travels to the reflective element through a first sub-projection optical path and is further reflected to the to-be-scanned object from the reflective element through a second sub-projection optical path; the imaging light is reflected to the reflective element from the to-be-scanned object through a first sub-imaging optical path and is further reflected to the image sensing element from the reflective element through a second sub-imaging optical path;
 wherein the single polarity element is located on the second sub-projection optical path and the first sub-imaging optical path.

16. A three-dimensional contour scanning device, comprising:
 an image sensing element;
 a light source used for emitting a projection light to a to-be-scanned object through a projection optical path, wherein the projection light reflected from the to-be-scanned object becomes an imaging light and to the image sensing element through an image-formed optical path; and
 a single polarity element disposed on the projection optical path and the image-formed optical path;
 wherein the three-dimensional contour scanning device further comprises:
 a reflective element located on the projection optical path and the image-formed optical path;
 wherein the projection light travels to the reflective element through a first sub-projection optical path and is further reflected to the to-be-scanned object from the reflective element through a second sub-projection optical path; the imaging light is reflected to the reflective element from the to-be-scanned object through a first sub-imaging optical path and is further reflected to the image sensing element from the reflective element through a second sub-imaging optical path;

wherein the single polarity element is located on the first sub-projection optical path, the second sub-projection optical path, the first sub-imaging optical path and the second sub-imaging optical path.

17. A three-dimensional contour scanning device, comprising:

an image sensing element;

a light source used for emitting a projection light to a to-be-scanned object through a projection optical path, wherein the projection light reflected from the to-be-scanned object becomes an imaging light and to the image sensing element through an image-formed optical path; and a single polarity element disposed on the projection optical path and the image-formed optical path;

wherein the three-dimensional contour scanning device further comprises:

a reflective element located on the projection optical path and the image-formed optical path;

wherein the projection light travels to the reflective element through a first sub-projection optical path and is further reflected to the to-be-scanned object from the reflective element through a second sub-projection optical path; the imaging light is reflected to the reflective element from the to-be-scanned object through a first sub-imaging optical path and is further reflected to the image sensing element from the reflective element through a second sub-imaging optical path;

wherein an angle included between the first sub-projection optical path and the second sub-imaging optical path is smaller than 15°.

* * * * *